United States Patent [19]

Baldi et al.

[11] 4,232,153

[45] Nov. 4, 1980

[54] PROCESS FOR THE PRODUCTION OF CHLORO-DI (ALKYLAMINO)-s-TRIAZINES

[75] Inventors: Luciano Baldi; Renato Francese, both of Turin; Franco Collecchia, Borgaro, all of Italy

[73] Assignee: Rumianca S.p.A., Turin, Italy

[21] Appl. No.: 922,698

[22] Filed: Jul. 7, 1978

[30] Foreign Application Priority Data

Jul. 7, 1977 [IT] Italy .............................. 25474 A/77

[51] Int. Cl.³ .......................................... C07D 251/50
[52] U.S. Cl. ..................................................... 544/204
[58] Field of Search ........................................ 544/204

[56] References Cited

U.S. PATENT DOCUMENTS

| | | | |
|---|---|---|---|
| 3,436,394 | 4/1969 | Saul | 544/204 |
| 3,590,040 | 6/1971 | Ferguson et al. | 544/204 |
| 3,639,399 | 2/1972 | Daugherty et al. | 544/204 |
| 4,054,739 | 10/1977 | Haschke et al. | 544/204 |
| 4,058,662 | 11/1977 | Haschke et al. | 544/204 |
| 4,099,006 | 7/1978 | Baldi et al. | 544/204 |

*Primary Examiner*—John M. Ford
*Attorney, Agent, or Firm*—Sughrue, Rothwell, Mion, Zinn and Macpeak

[57] ABSTRACT

Chloro-bis(alkylamino)-s-triazines are prepared by stepwise replacement of two chlorine atoms of cyanuric chloride with alkylamino groups.

Cyanuric chloride, an inorganic base and an alkylamine are continuously fed to a first tubular zone in stoichiometric proportions and reacted therein under turbulent conditions, at an elevated temperature not exceeding 90° C., and for a short reaction time, and the reaction product is continuously fed to a second tubular reaction zone together with stoichiometric quantities of inorganic base and of a second alkylamine, and reacted therein with the latter at an elevated temperature not exceeding 100° C., under turbulent conditions and for a short reaction time.

22 Claims, No Drawings

PROCESS FOR THE PRODUCTION OF CHLORO-DI (ALKYLAMINO)-s-TRIAZINES

The present invention relates to the preparation of chloro-di(alkylamino)-s-triazines by means of a continuous process. The chloro-di(alkylamino)-s-triazines are compounds given by the general formula:

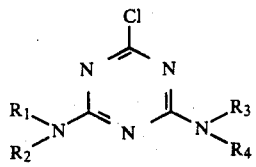

where $R_1$, $R_2$, $R_3$ and $R_4$ independently are an atom of hydrogen or an alkyl radical containing from 1 to 5 carbon atoms and possibly also certain other functional groups.

The chloro-di(alkylamino)-s-triazines are valued herbicides and the most noted compounds belonging to this group are: 2-chloro-4-ethylamino-6-isopropylamino-s-triazine(atrazine), 2-chloro-4,6-di(ethylamino)-s-triazine (simazine) and 2-chloro-4,6-di(isopropylamino)-s-triazine (propazine).

The herbicidal characteristics of these compounds are described in U.S. Pat. No. 2,891,855 here cited as a reference.

The chloro-di(alkylamino)-s-triazines are generally prepared from cyanuric chloride by successive substitution of two chlorine atoms with primary or secondary alkylamino groups, as described, for example, by W. Pearlman and C. K. Banks in J.Am.Chem.Soc.70, 3726 (1948). In practice the reaction is carried out according to the general scheme:

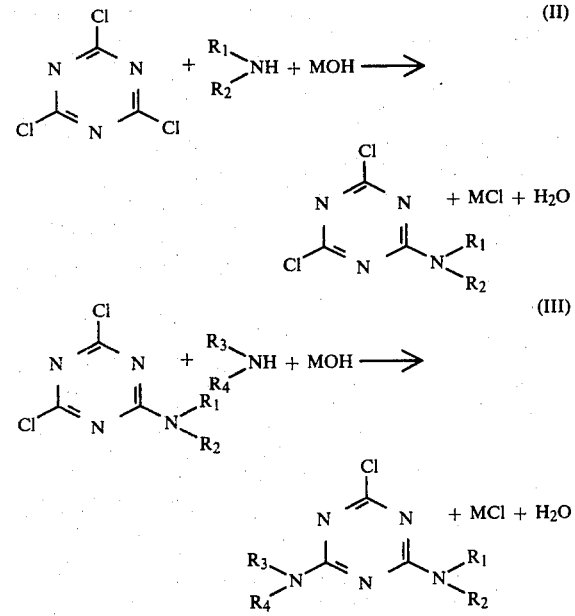

where M represents an alkali metal. In particular the preparation of atrazine is carried out in discontinuous stages by reacting, in a first reaction stage, cyanuric chloride with isopropylamine, in the presence of sodium hydroxide, to give 2,4-dichloro-6-isopropylamino-s-triazine. This latter is reacted in a second stage with ethylamine and with a further quantity of sodium hydroxide, with subsequent formation of the desired product: 2-chloro-4-ethylamino-6-isopropylamino-s-triazine.

Various devices have been adopted in the art in the process for the preparation of chloro-di(alkylamino)-s-triazines, especially with regard to the composition of the medium in which the reaction is carried out.

Thus, for example, it has been proposed to carry out the reaction in an aqueous medium in the presence of a surface active agent designed to maintain the cyanuric chloride in suspension in the form of a subdivided solid. Such reactive systems are unsuitable for application on a commercial scale, especially in view of the low reaction rates obtainable.

It is also known to carry out the reaction in single-phase water-organic compound mixtures, for example in water-acetone and water-dioxan mixtures, using an organic compound which dissolves the cyanuric chloride and is miscible with water in all proportions. This procedure has disadvantages resulting essentially from the formation of undesirable by-products, such as, for example, tri(alkylamino)-s-triazine and hydrolysis products, with consequent notable lowering of the yield of the desired reaction product. Hence the purification of the latter is difficult and the said procedure is uneconomic. In order to improve the yield it has been proposed to carry out the reaction at temperatures of from 0° C. to −15° C., to minimise the hydrolysis phenomena. Such a method requires long reaction times and presents not insignificant problems in the application on a commercial scale.

It is also known to resort to two-phase water-organic compound mixtures such as water-chlorobenzene, water-carbon tetrachloride and water-toluene, using an organic compound which dissolves the cyanuric chloride and is practically immiscible with water. Such systems have disadvantages due not only to the relatively low reaction kinetics but also the low temperatures required to avoid the formation of undesirable by-products.

There have also been proposed in the art, aqueous two-phase mixtures such as water-methyl ethyl ketone, water-methyl propyl ketone and water-diethyl ketone, using an organic compound which dissolves the cyanuric chloride and is only partly soluble in water. In this case also hydrolysis phenomena of the cyanuric chloride easily occur, given the presence of water in the reaction medium and consequently low reaction temperatures, in general lower than 0° C., are needed. This deleteriously affects the simplicity and the economics of the process.

Finally, the adoption of non-aqueous systems for the preparation of the compounds under discussion has not given satisfactory results, in that there are no known commercial scale processes based on such a technique.

Hence the known art does not allow of the production of chloro-di(alkylamino)-s-triazines with high values of the yield and of the selectivity, in systems operating with high reaction kinetics. Above all of these desirable results have not been obtained by using a continuous method which is simple and easy to use. It must be considered on the other hand that a continuous process presents potentially, with respect to discontinuous processes, a greater yield in the time per unit of useful volume of the reactor, greater possibility of automation of the plant and a greater constancy of the characteristics of the product obtained. Up till now the difficulties described above have prevented the realisation of advantageous processes for the continuous production of chloro-di(alkylamino)-s-triazines.

The object of the present invention is, therefore, to surmount these difficulties of the known art. The present invention is based essentially on the evidence that the reactions (II) and (III) given above, take place at high speeds, substantially up to completion and with little formation of by-products in a tubular reaction zone in which the reagent mass is maintained in a turbulent condition and at a relatively high temperature.

Thus, the invention provides a continuous process for the preparation of chloro-bis(alkylamino)-s-triazine by means of the step-wise replacement of two chlorine atoms of cyanuric chloride with alkylamino groups, characterized by (a) continuously feeding cyanuric chloride in the form of a solution in an organic solvent to the inlet end of a first tubular reaction zone, continuously feeding an inorganic base, a first alkylamine and water to said first tubular reaction zone, said inorganic base and said first alkylamine being fed in at least in part at the inlet end of said first reaction zone, said cyanuric chloride, inorganic base and first alkylamine being fed in in substantially stoichiometric proportions and reacted in said first reaction zone under turbulent conditions and at a temperature not exceeding 90° C. to convert substantially completely said cyanuric chloride to 2,4-di-chloro-6-alkylamino-6-triazine, and continuously discharging the reaction product of (a) from the outlet end of said first tubular reaction zone;

(b) continuously feeding said reaction product of (a), upon possible cooling and possible removal of aqueous phase from said reaction product of (a), to the inlet end of a second tubular reaction zone, continuously feeding to said second reaction zone an inorganic base, a second alkylamine and water, said inorganic base of (b) and said second alkylamine being fed in at least in part at the inlet end of said second tubular reaction zone, said 2,4-di-chloro-6-alkylamino-s-triazine, inorganic base of (b) and second alkylamine being fed in in substantially stoichiometric proportions and reacted in said second reaction zone under turbulent conditions and at a temperature not exceeding 100° C. to convert substantially completely said 2,4-di-chloro-6-alkylamino-s-triazine into chloro-bis(alkylamino)-s-triazine; and (c) continuously discharging the reaction product of (b) from the second reaction zone and recovering the chloro-bis(alkylamino)-s-triazine from said reaction product of (b).

The stages (a) and (b) can be carried out in two separate tubular reactors with possible removal of material and/or of heat between one stage and the other. According to a preferred embodiment, a single tubular reactor is used and no intermediate removal of material takes place. In such an embodiment the cyanuric chloride is fed continuously to the inlet end of the reactor together with the quantity of the other reagents necessary for the formation of the 2,4-dichloro-6-alkylamino-s-triazine. The reagents necessary for the formation of the chloro-di(alkylamino)-s-triazine are fed continuously to a suitable intermediate position of the reactor. The reaction products are discharged continuously from the outlet end of the reactor and are subjected to the usual treatments for the separation of the chloro-di(alkylamino)-s-triazine. It would also be possible, in the case of a single reactor, to provide intermediate cooling of the mass between the two reaction stages. Moreover it is also possible to feed the amine and the inorganic base partly to the inlet end of the tubular reaction zone and partly to one or more points along said tubular reaction zone. This can obviously be achieved for a single stage, or for both the stages, both in the case of a single reactor and in the case of two separate reactors.

The organic solvents which are suitable for the purpose are those which are inert under the reaction conditions and have good solvating power for the cyanuric chloride. Examples of suitable organic solvents are diethyl ether, dioxan, diethyl cellosolve, benzene, toluene, xylene, chlorobenzene, acetone, methyl ethyl ketone, carbon tetrachloride, or such other organic solvents known in the art in respect of the preparation of the chloro-di(alkylamino)-s-triazines. The organic solvents forming a single-phase system or a two-phase system with water may be used in the process of the invention. Examples of single-phase systems are water-acetone and water-dioxan and examples of two-phase systems are water-benzene and water-chlorobenzene. In practice, the cyanuric chloride, dissolved in the organic solvent, is fed to the first tubular reaction zone and the inorganic base and the amine are fed in the form of one or more aqueous solutions.

In the case in which the amine is insoluble or scarcely soluble in water an independent feed for the said amine may be provided.

According to the present invention, the medium in which the reaction is carried out is not as important as the maintenance of a high reaction kinetics in a reagent system such as that described above.

To this end stage (a) may be carried under isothermal conditions, at a temperature of from 30° to 90° C., or under adiabatic conditions with a maximum temperature not greater than 90° C.

When operating under isothermal conditions a heat exchanger, designed to maintain the temperature in the tubular reaction zone between the said limits, may be provided. When operating under adiabatic conditions it is understood that there is no heat exchanger so that the temperature rises from the inlet value up to the said maximum temperature or that the said increase in temperature is controlled by means of differential exchange in the various zones of the reactor.

When the reaction is carried out adiabatically the inlet temperature of the reagents is not important in that the reaction is initiated easily, even at relatively low temperatures, with subsequent rapid increase in the temperature. The said reagents are conveniently fed in at ambient temperature even if it possible to use inlet temperatures greater or lower than the ambient temperature.

Stage (b) may be carried out under isothermal conditions at a temperature of from 40°–50° C. to 100° C. or under adiabatic conditions, in the sense given above, with a maximum temperature not greater than 100° C. When the reaction is carried out under adiabatic conditions the input temperature in stage (b) is generally maintained at a value of at least 20°–30° C. The control of this input temperature may be effected by means of a heat exchanger placed between the two reaction stages, or else by means of the aqueous solution of the inorganic base and of the amine fed into stage (b). Obviously it is possible to influence simultaneously the temperature by means of the two factors mentioned above.

Generally the reaction is carried out without applying any overpressure or else the overpressure necessary to maintain the reaction mass in the liquid phase at the reaction temperature is applied.

Under the conditions described the reactions of stages (a) and (b) are completed or substantially completed in a time of the order of a few minutes and in every case in a time less than about ten minutes.

The chloro-di(alkylamino)-s-triazines thus obtained have a purity of 99% or more which demonostrates the low formation of by-products. It is considered, therefore, that the operation at relatively high temperatures and hence with high reaction speeds, in a reactive system such as that of the present invention, favours the formation of the desired reaction product, whereas it is usual in the known art to use low temperatures for the purpose of minimising the formation of by-products. Moreover, it must be considered that in the process of the present invention, the medium in which the reaction is carried out is not particularly critical in that desirable results are obtained both with single-phase and two-phase water-organic solvent systems, whereas in the processes of the known art the reaction medium influences the course of the said reaction noticeably.

By means of the process of the present invention all the compounds definable by means of the general formula (1), in which $R_1$, $R_2$, $R_3$ and $R_4$ independently are hydrogen or linear or branched or even cyclic alkyl radicals, either the same or different from each other, having from 1 to 5 atoms of carbon may be prepared. Examples of such alkyl radicals are: methyl, ethyl, isopropyl, cyclopropyl, n-butyl, sec.-butyl and tert-butyl. However, in the following description specific reference will be made to the preparation of 2-chloro-4-ethylamino-6-isopropylamino-s-triazine.

This is for the sake of simplicity, taking account of the fact that wholly similar considerations prevail for the other chloro-di(alkylamino)-s-triazines.

STAGE (A)

In this stage there are loaded into the first tubular reaction zone: cyanuric chloride, isopropylamine and sodium hydroxide to produce 2,4-dichloro-6-isopropylamino-s-triazine according to the reaction:

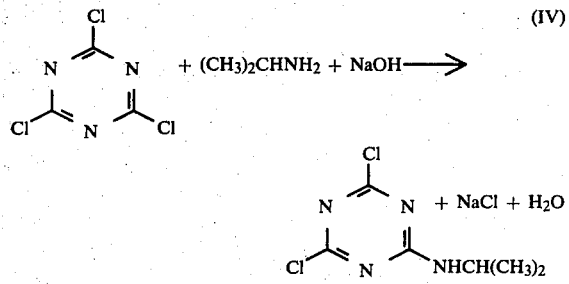

The quantities of isopropylamine and of sodium hydroxide are equivalent, or nearly equivalent, to those needed for the formation of 2,4-dichloro-6-isopropylamino-s-triazine. Instead of sodium hydroxide, sodium carbonate, or the hydroxide or carbonate of other alkali metals such as lithium and potassium, may be used. According to a preferred embodiment, isoprolymamine is used in an excess such as to neutralise the hydrogen chloride which is formed in the reaction.

The cyanuric chloride is, as a rule, fed in in the form of a solution in the pre-selected organic solvent. The organic solvents which are preferred for the purpose are those mentioned previously since, as well as the said characteristics, they are readily separable, for example by distillation, from the final product of the reaction.

The inorganic base and the amine are conveniently fed in in the form of one or more aqueous solutions.

The quantities of organic solvents and of water fed into the reaction medium are not particularly critical; it is, moreover, convenient to maintain a ratio by weight between the two of from 3:1 to 3:2. Good results are obtained, moreover, by regulating the feeds in such a way that the concentration of the 2,4-dichloro-6-isopropylamino-s-triazine is of the order of 10 to 20% by weight with respect to the organic solvent in the product discharged from stage (a).

Reactors useful for the purposes of the present invention are those elongate, tubular reactors in which the length/diameter ratio is high, for example, greater than about 2/1. Moreover according to a basic aspect of the present invention, the reaction mass is maintained in turbulent conditions, for example by suitable choice of the diameter of the reactor and of the velocity of the reagent mass, by using an agitator, or by introduction into the reactor of filling bodies (of spherical, helical or other form), of partial diaphragms, of foraminous plates and so on. Obviously it is possible to operate on one or more of these factors. Thus, for example, in a reactor with a diameter of 2-3 cm, provided with filling bodies, a linear velocity of the reagent mass greater than about 0.5 meters/second is maintained in the case of a single-phase system. In the case of a two-phase system it is convenient to ensure dimensions of the dispersed phase of less than 100 microns and preferably less than 10 microns. For this purpose one may also resort to the addition of surface active agents, together with the reagents, to the reaction medium.

As has already been stated the reaction may be carried out under isothermal or adiabatic conditions. In the first case excellent results are obtained with temperatures of the order of 40°-60° C. and in the second case with maximum temperatures not exceeding 60°-70° C. and preferably of the order of 55°-60° C. When the reaction is carried out adiabatically the reagents and the reaction medium are conveniently fed in at the ambient temperature.

By operating under the conditions described, the reaction time is generally from about 20 seconds to about 2 minutes and the reaction mass is conveyed to the second reactor, or to the second portion of the single reactor, after possible cooling. In the case in which the reaction is carried out with two separate reactors it is also possible to separate material such as, for example, the aqueous phase.

STAGE (B)

In stage (b) there are loaded into the second tubular reaction zone the 2,4-dichloro-6-isopropylamino-s-triazine coming from stage (a), ethylamine and sodium hydroxide to produce 2-chloro-4-ethylamino-6-isopropylamino-s-triazine according to the reaction:

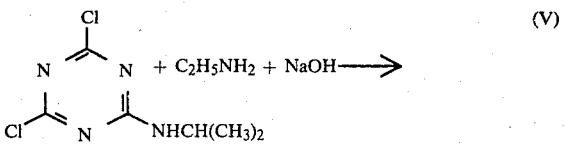

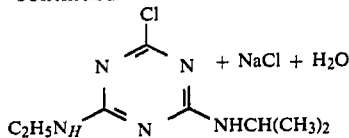

The quantities of ethylamine and of sodium hydroxide are equivalent or about equivalent to those needed to the formation of the 2-chloro-4-ethylamino-6-isopropylamino-s-triazine. As has been stated, the product of the reaction is preferably fed in as it comes from stage (a). The ethylamine and the sodium hydroxide are conveniently fed in in the form of one or more aqueous solutions.

Stage (b) may also be carried out under isothermal or adiabatic conditions. In the first case the temperature is preferably of the order of 50°–80° C. and in the second case the maximum temperature is advantageously kept at a value not exceeding 70°–80° C. and preferably at a value of about 65°–75° C. Moreover when the reaction is carried out adiabatically it is convenient to keep the input temperature of stage (b) at a value of the order of 40°–50° C. According to one aspect of the present invention, stage (b) is carried out within a range of temperatures less than those corresponding to the solubility of the reaction product in the reaction medium, with the absence of precipitation depending essentially on the short reactions periods necessary. The operation with safety in conditions of supersaturation allows the avoidance of those excessively high temperatures which would endanger the reaction yield and the quality of the desired product. The range of temperatures within which it is possible to carry out the reaction without precipitation in the case of the production of 2-chloro-4-ethylamino-6-isopropylamino-s-triazine in a water-toluene medium, varies from a minimum of 40°–60° C. up to a maximum of 80°–90° C., depending on the concentration of the said 2-chloro-4- ethylamine-6-isopropylamino-s-triazine. In every case the said temperature range for supersaturation, between which precipitation does not occur when operating according to the present invention, varies for each chloro-di(alkylamino)-s-triazine as a function of the concentration of the said compound and the nature and composition of the reaction medium.

It is possible, even if not convenient, to carry out the reaction in temperature conditions at which the said precipitation occurs. In these circumstances it is convenient to resort to the aid of wetting of dispersing agents such as aluminium lignin sulphonate so as not to obstruct the reactor. The other conditions for stage (b) are entirely similar to those for stage (a). The reaction time in stage (b) is generally of the order of 1–5 minutes.

STAGE (C)

The reaction mixture is discharged at the outlet of the second reaction zone is subjected to the usual treatment for the separation of the 2-chloro-4-ethylamino-6-isopropylamino-s-triazine. Generally this mixture is conveyed, without being cooled, to apparatus for its distillation and the recovery of the organic solvent. The distillation residue, in the form of a dense suspension, is subjected to treatments, according to known industrial techniques, for the separation of the desired reaction product.

By operating in the manner described, the reaction yield is generally of at least 98% with respect to the cyanuric chloride, with a purity of the desired reaction product of at least 99%.

EXAMPLE 1

A reactor consisting of a stainless-steel tube having a length of 10 meters, an internal diameter of 4 mm and an external diameter of 6 mm, is used. The tube is filled with sand grains, 1.2–1.8 mm in size, having a bulk density of 1.48 g/cm$^3$ and a relative density of 2.6 g/cm$^3$. The first 2.5 meters of the reactor are intended for the formation of the 2,4-dichloro-6-alkylamino-s-triazine (first reaction zone; stage (a)) and the remaining part is intended for the formation of the chloro-di(alkylamino)-s-triazine (second reaction zone; stage (b)). More particularly, to the inlet end of the first reaction zone there are fed 43 ml/min of a toluene solution containing 15% by weight of cyanuric chloride and, separately, 13.8 ml/min of an aqueous solution containing 12.77% by weight of isopropylamine and 8.85% by weight of sodium hydroxide. In this way the molar ratio between cyanuric chloride, isopropylamine and sodium hydroxide at the input to stage (a) is equal to 1:1:1. Moreover, the reaction of stage (a) is carried out adiabatically with an inlet temperature of the reaction mixture of 18° C. and with an outlet temperature of the said mixture of 55° C. No heat exchange is carried out between the two reaction stages and at the inlet to stage (b) there is fed 11.1 ml/min of an aqueous solution containing 12.15% by weight of monoethylamine and 11.25% by weight of sodium hydroxide. This solution is fed in at a temperature of 18° C. Stage (b) is also carried adiabatically and the temperature of the mass discharged from the reactor is 70° C. 2-chloro-4-ethylamino-6-isopropylamino-s-triazine is separated from the reaction product with a purity of 99%. The reaction yield evaluated with respect to the cyanuric chloride is equal to 98%.

EXAMPLE 2

This test is carried out as in Example 1, delivering to the inlet end of the first reaction zone 37 ml/min of a solution containing 16% by weight of cyanuric chloride in methyl ethyl ketone and, independently, 13.8 ml/min of an aqueous solution containing 12.77% by weight of isopropylamine and 8.85% by weight of sodium hydroxide. The molar ratio in the feed between cyanuric chloride, isopropylamine and sodium hydroxide is thus equal to 1:1:1.

The inlet temperature of stage (a) is equal to 18° C. and the outlet temperature is 58° C.

At the inlet end of the second reaction zone there are fed 11.1 ml/min of an aqueous solution containing 12.15% by weight of monoethylamine and 11.25% by weight of sodium hydroxide. The temperature of the reaction mass at the outlet from the reactor is 70° C.

2-chloro-4-ethylamino-6-isopropylamino-s-triazine is recovered from the reaction products with a purity of 99%. The yield evaluated as in Example 1 is 98%.

EXAMPLE 3

This test is carried out in a tubular reactor provided with filling bodies, in which the reaction volume in stage (a) is 12 liters and that in stage (b) is 36 liters. The volume is evaluated in the absence of the filling bodies. At the input to stage (a) there are fed 1317 Kg/hour of a toluene solution containing 14% by weight of cyanuric chloride and 492 Kg/hour of an aqueous solution containing 12% by weight of isopropylamine and 8.12% by weight of sodium hydroxide. The reaction of stage (a) is carried out in adiabatic conditions, with an inlet temperature of 18° C. and with an outlet temperature of 60° C. At the input to stage (b) there is fed 375 Kg/hour of an aqueous solution containing 12% by weight of monoethylamine and 10.64% by weight of sodium hydrozide.

No heat exchange is carried out between the two stages and the reaction mixture leaving the reactor has a temperature of 75° C.

2-chloro-4-ethylamino-6-isopropylamino-s-triazine is separated from the reaction products with a purity of 99%. The reaction yield is 99.5%, based on cyanuric chloride.

EXAMPLE 4

This test is carried out as in Example 3, feeding to the inlet end of the tubular reactor 1317 Kg/hour of solution containing 16% by weight of cyanuric chloride in methyl ethyl ketone and 562 Kg/hour of an aqueous solution containing 12% by weight of isopropylamine and 8.12% by weight of sodium hydroxide. Stage (a) is carried out adiabatically with an inlet temperature of 18° C. and an outlet temperature of 57° C. To the input of stage (b) there is fed 492 Kg/hour of an aqueous solution containing 12% by weight of monoethylamine and 10.64% by weight of sodium hydroxide. Stage (b) is carried out under adiabatic conditions, the temperature of the reaction mass at the outlet from the reaction being 65° C. 2-chloro-4-ethylamino-6-isopropylamino-s-triazine is separated with a purity of 99%. The reaction yield is 99% based on cyanuric chloride.

EXAMPLE 5

This test is carried out as in Example 3, feeding to the inlet end of the reactor 1317 Kg/hour of a solution containing 14% by weight of cyanuric chloride in acetone and 492 Kg/hour of an aqueous solution containing 12% by weight of isopropylamine and 8.12% by weight of sodium hydroxide. The inlet temperature of stage (a) is 18° C. and the outlet temperature is 55° C. Stage (b) is carried out under isothermal conditions with a temperature of 55° C. and for this purpose the corresponding part of the reactor is provided with heat exchange means. To the input of stage (b) there is fed 375 Kg/hour of an aqueous solution containing 12% by weight of monoethylamine and 10.64% by weight of sodium hydroxide. The reaction products are recovered at the outlet end of the reactor. The conversion of cyanuric chloride is 99% and the 2-chloro-4-ethylamino-6-isopropylamino-s-triazine thus obtained has a purity of 99%.

We claim:

1. In a process for the preparation of chloro-bis(alkylamino)-s-triazine by means of stepwise replacement of two chlorine atoms of cyanuric chloride with alkylamino groups at a temperature not exceeding 90° C. during the first replacement of a chlorine atom and at a temperature not exceeding 100° C. during the second replacement of a chlorine atom, the improvement which comprises;

(a) continuously feeding cyanuric chloride in the form of a solution in an inorganic solvent to the inlet end of a first tubular reaction zone, continuously feeding an inorganic base, a first alkylamine and water to said first tubular reaction zone, said inorganic base and said first alkylamine being fed in at least in part at the inlet end of said first reaction zone, said cyanuric chloride, inorganic base and first alkylamine being fed in in substantially stoichiometric proportions and reacted in said first reaction zone under turbulent conditions to convert substantially completely said cyanuric chloride to 2,4-di-chloro-6-alkylamino-s-triazine, and continuously discharging the reaction product of (a) from the outlet end of said first tubular reaction zone;

(b) continuously feeding said reaction product of (a), upon possible cooling and possible removal of aqueous phase from said reaction product of (a), to the inlet end of a second tubular reaction zone, continuously feeding to said second reaction zone an inorganic base, a second alkylamine and water, said inorganic base of (b) and said second alkylamine being fed in at least in part at the inlet end of said second tubular reaction zone, said 2,4-di-chloro-6-alkylamino-s-triazine, inorganic base of (b) and second alkylamine being fed in in substantially stoichiometric proportions and reacted in said second reaction zone under turbulent conditions to convert substantially completely said 2,4-di-chloro-6-alkylamino-s-triazine into chloro-bis-(alkylamino)-s-triazine; and wherein the reaction times in said first and second reaction zones are less than 10 minutes; and (c) continuously discharging the reaction product of (b) from the second reaction zone and recovering the chloro-bis(alkylamino)-s-triazine from said reaction product of (b).

2. The process of claim 1, wherein stages (a) and (b) are carried out in a single tubular reactor, the reaction product of (a) being directly delivered to stage (b) upon possible cooling.

3. The process of claim 1, in which stage (a) is carried out under isothermal conditions at a temperature of from 30° to 90° C., and stage (b) under isothermal conditions at a temperature of from 40° to 100° C.

4. The process of claim 1, in which stage (a) is carried out under isothermal conditions at a temperature of from 40° to 60° C., and stage (b) under isothermal conditions at a temperature of from 50° to 80° C.

5. The process of claim 1, wherein the reaction time is from 20 seconds to 2 minutes in stage (a) and from 1 to 5 minutes in stage (b).

6. The process of claim 1, wherein said inorganic base used in (a) and (b) is chosen from the hydroxides and carbonates of sodium, potassium and lithium.

7. The process of claim 1, wherein said inorganic base is sodium hydroxide.

8. The process of claim 1, wherein said first and second tubular reaction zones have a length/diameter ratio of at least 2:1.

9. The process of claim 1, wherein said first and second reaction zones are provided with at least one of the group consisting of agitators, filling bodies, partial diaphragms and foraminous plates.

10. The process of claim 1, wherein said organic solvent forms a single-phase or a two-phase mixture with water.

11. The process of claim 1, wherein the organic solvent is removed from the reaction product of (b) by distillation, and the chloro-bis(alkylamino)-s-triazine is recovered from the resulting distillation residue.

12. The process of claim 1, wherein said chloro-bis(alkylamino)-s-triazine is 2-chloro-4-ethylamino-6-isopropylamino-s-triazine.

13. The process of claim 1, in which the whole of said inorganic base and amine reagents are added at the inlet end of each reaction zone.

14. The process of claim 1, in which stage (a) is carried out under adiabatic conditions with a maximum temperature not exceeding 90° C., and stage (b) under adiabatic conditions with an inlet temperature of at least 20° C. and a maximum temperature not exceeding 100° C.

15. The process of claim 1, in which stage (a) is carried out under adiabatic conditions with a maximum temperature not exceeding 70° C., and stage (b) under adiabatic conditions with an inlet temperature of at least 40° C. and a maximum temperature not exceeding 80° C.

16. The process of claim 1, in which stage (a) is carried out under isothermal conditions at a temperature of 30° C. to 90° C., and stage (b) under adiabatic conditions with an inlet temperature of at least 20° C. and a maximum temperature not exceeding 100° C.

17. The process of claim 1, in which stage (a) is carried out under adiabatic conditions with a maximum temperature not exceeding 90° C., and stage (b) under isothermal conditions at a temperature of 40° C. to 100° C.

18. The process of claim 1, in which stage (a) is carried out under isothermal conditions at a temperature of from 40° C. to 60° C., and stage (b) under adiabatic conditions with an inlet temperature of at least 40° C. and a maximum temperature not exceeding 80° C.

19. The process of claim 1, in which stage (a) is carried out under adiabatic conditions with a maximum temperature not exceeding 70° C., and stage (b) under isothermal conditions at a temperature of 50° C. to 80° C.

20. The process of claim 16, wherein said maximum temperature in stage (a) is from 55° C. to 60° C. and said maximum temperature in stage (b) is from 65° C. to 75° C.

21. The process of claim 19, wherein said maximum temperature in stage (b) is from 65° C. to 75° C.

22. The process of claim 20, wherein said maximum temperature in stage (a) is from 55° C. to 60° C.

* * * * *